(12) United States Patent
Waldvogel et al.

(10) Patent No.: US 8,603,270 B2
(45) Date of Patent: Dec. 10, 2013

(54) ODOR SAMPLES OF PEROXIDIC EXPLOSIVES

(75) Inventors: Siegfried Waldvogel, Ingelheim (DE); Carsten Siering, Mainz (DE); Daniel Lubczyk, Mainz (DE); Joerg Loebau, Heiligenberg (DE); Arno Hahma, Henfenfeld (DE)

(73) Assignees: Rheinische Friedrich-Wilhelms-Universitaet Bonn, Bonn (DE); Diehl BGT, Defence GmbH & Co. KG, Ueberlingen (DE)

( * ) Notice: Subject to any disclaimer, the term of this patent is extended or adjusted under 35 U.S.C. 154(b) by 10 days.

(21) Appl. No.: 13/378,049

(22) PCT Filed: Jun. 18, 2010

(86) PCT No.: PCT/EP2010/058660
§ 371 (c)(1),
(2), (4) Date: Dec. 14, 2011

(87) PCT Pub. No.: WO2010/146170
PCT Pub. Date: Dec. 23, 2010

(65) Prior Publication Data
US 2012/0090744 A1    Apr. 19, 2012

(30) Foreign Application Priority Data
Jun. 18, 2009 (DE) .......... 10 2009 029 787

(51) Int. Cl.
*C06B 45/00* (2006.01)
*D03D 23/00* (2006.01)
*D03D 43/00* (2006.01)

(52) U.S. Cl.
USPC ...... 149/109.6; 149/2; 149/108.4; 149/108.8; 149/109.4

(58) Field of Classification Search
USPC .......... 149/108.8, 2, 108.4, 109.4, 109.6
See application file for complete search history.

(56) References Cited

U.S. PATENT DOCUMENTS

| | | |
|---|---|---|
| 3,538,011 A | 11/1970 | van der Klaauw |
| 4,455,252 A | 6/1984 | Wylegala et al. |
| 5,648,636 A | 7/1997 | Simpson et al. |

(Continued)

FOREIGN PATENT DOCUMENTS

| | | |
|---|---|---|
| WO | WO 2004/035018 A2 | 4/2004 |
| WO | WO 2007/005471 A2 | 1/2007 |

OTHER PUBLICATIONS

S. Baj et al.: "A new method for dialkyl peroxides synthesis in ionic liquids as solvents", Green Chemistry, vol. 8, pp. 292-295 (2006); XP-002613529.

(Continued)

*Primary Examiner* — James McDonough
(74) *Attorney, Agent, or Firm* — Norman B. Thot

(57) ABSTRACT

The present invention provides a method of using a neutral ionic liquid to at least one of stabilize a peroxidic explosive and to produce a stable solution of the peroxidic explosive which includes providing the neutral ionic liquid and using the neutral ionic liquid to at least one of stabilize the peroxidic explosive and to produce the stable solution of the peroxidic explosive. The present invention further provides a stable composition which includes a solution of at least one neutral ionic liquid and a detectable amount of a peroxidic explosive, a method of production thereof, and a method of use thereof as an odor sample.

9 Claims, 2 Drawing Sheets

(56) References Cited

U.S. PATENT DOCUMENTS

| | | | |
|---|---|---|---|
| 6,767,717 | B1 | 7/2004 | Itzhaky et al. |
| 7,998,615 | B2* | 8/2011 | Matsui et al. ............... 429/199 |
| 8,012,277 | B2* | 9/2011 | Nicolich et al. ............... 149/22 |
| 2006/0135822 | A1 | 6/2006 | Schwarz et al. |
| 2006/0166856 | A1* | 7/2006 | Petrat et al. ..................... 512/2 |
| 2006/0183654 | A1 | 8/2006 | Small |
| 2008/0248578 | A1* | 10/2008 | Deans et al. ..................... 436/8 |
| 2008/0251169 | A1* | 10/2008 | Nicolich et al. ............... 149/22 |
| 2009/0199936 | A1* | 8/2009 | Hagit et al. ................... 149/33 |
| 2011/0315283 | A1* | 12/2011 | Hagit et al. ............... 149/109.4 |
| 2013/0109103 | A1* | 5/2013 | Waldvogel et al. ............ 436/92 |

OTHER PUBLICATIONS

S. L. Jain et al.: "[Bmim]BF4-immobilized rhenium-catalyzed highly efficient oxygenation of aldimines to oxaziridines using solid peroxides as oxidants", Journal of Organometallic Chemistry, vol. 692, pp. 2930-2935 (2007); XP-002613530.

S. Pandey: "Analytical applications of room-temperature ionic liquids: A review of recent efforts", Analytica Chimica Acta, vol. 556, pp. 38-45 (2006); XP-002613531.

A. Miyake et al.: "Mixing hazard evaluation of organic peroxides with other chemicals", Journal of Loss Prevention in the Process Industries, vol. 18, pp. 380-383 (2005); XP-002613532.

R. P. Singh et al.: "Energetic Nitrogen-Rich Salts and Ionic Liquids", Angewandte Chemie, International Edition, vol. 45, pp. 3584-3601 (2006); XP-002613533.

R. Meyer et al.: Explosives, Wiley-VCH, Weinheim, p. 346 (2002).

J. C. Oxley et al.: "Determination of the Vapor Density of Triacetone Triperoxide (TATP) Using a Gas Chromatography Headspace Technique", Propellants, Explosives, Pyrotechnics 30, No. 2, pp. 127-130 (2005).

EMPK: Bundesanstalt f. Materialforschung und—prüfung AZ: II.3/4726/04 and certification by Wehrwissenschaftliches Institut für Werk-, Explosiv- und Betriebsstoffe (WIWEB) Doc. No. 330/27454/04.

Eds: H. Schubert, A. Kuznetsov: "Detection of Liquid Explosives and Flammable Agents in Connection with Terrorism", Published by Springer, pp. 36-38, 71-78, 123-132, (2008).

R. Schulte-Ladbeck et al.: "Recent methods for the determination of peroxide-based explosives", Anal Bioanal Chem 386: 559-565 (2006).

R. A. A. Munoz et al.: "'One-step' simplified electrochemical sensing of TATP based on its acid treatment", Analyst 132, pp. 560-565 (2007).

D. Lu et al.: "Highly sensitive electrochemical detection of trace liquid peroxide explosives at a Prussian-blue 'artificial-peroxidase' modified electrode", Analyst 131, pp. 1279-1281 (2006).

D. F. Laine: "Electrochemical detection of triacetone triperoxide employing the electrocatalytic reaction of iron(II/III)-ethylenediaminetetraacetate and hydrogen peroxide", Analytica Chimica Acta 608, pp. 56-60 (2008).

R- Schulte-Ladbeck et al.: "A field test for the detection of peroxide-based explosives", Analyst 127, pp. 1152-1154 (2002).

M. E. Germain et al.: "Turn-on Fluorescence Detection of $H_2O_2$ and TATP", Inorganic Chemistry, vol. 47, No. 21, pp. 9748-9750 (2008).

S. Malashikhin et al.: "Fluorescent Signaling Based on Sulfoxide Profluorophores: Application to the Visual Detection of the Explosive TATP", J. Am. Chem. Soc. 130, pp. 12846-12847 (2008).

E. Sella et al.: "Self-immolative dendritic probe for direct detection of triacetone triperoxide", Chem. Commun., pp. 5701-5703 (2008).

Eds. P: Wasserscheidt, T. Welton: "Ionic Liquids in Synthesis", Wiley-VCH, Weinheim, p. 43 (2003).

http://www.accustandard.com; catalogue No. M-8330-ADD24, 0.1 mg TATP in 1 ml $CH_3CN$.

* cited by examiner

ODOR SAMPLES OF PEROXIDIC EXPLOSIVES

CROSS REFERENCE TO PRIOR APPLICATIONS

This application is a U.S. National Phase application under 35 U.S.C. §371 of International Application No. PCT/EP2010/058660, filed on Jun. 18, 2010 and which claims benefit to German Patent Application No. 10 2009 029 787.1, filed on Jun. 18, 2009. The International Application was published in German on Dec. 23, 2010 as WO 2010/146170 A2 under PCT Article 21(2).

FIELD

The invention provides the use of a neutral ionic liquid for stabilizing peroxidic explosives and for producing stable solutions of peroxidic explosives. The invention further provides stable compositions comprising a solution of a neutral ionic liquid and a detectable amount of a peroxidic explosive, the production thereof and use as odor samples.

BACKGROUND

Peroxidic explosives such as TATP or HMTD are "self elaborates" which can easily be produced in a large quantity from household chemicals. The high brisance and thus poor handleability for even small amounts of this material presents a safety challenge for the provision of samples of the genuine material. Peroxidic explosives such as TATP can be handled safely as solutions in lipophilic ionic liquids. The virtually constant evaporation rate of the peroxidic explosive can be utilized to simulate the odor profile of a larger explosive charge. The use for calibration purposes is likewise conceivable. The nonmeasurable vapor pressure of the ionic liquid does not influence the sample quality. The dissolution of the peroxidic explosive in combination with a reducing component in the ionic liquid permanently deactivates the explosive and can be used for desensitization.

The training of sniffer dogs and the calibration of measuring instruments have to be carried out using the genuine material. Substitutes cannot be used for this reason. Triacetone triperoxide (TATP) can be obtained in the synthesis as TATP hydrate which is easier to handle and has a slightly lower brisance. On the other hand, pure TATP is virtually unusable because of the friction- and shock-sensitivity and ignition by electrostatic charges as described by R. Meyer et al., in Explosives, 6th Ed. Wiley-VCH, Weinheim (2007) and J. C. Oxley et al., Propellants, Explosives, Pyrotechnics 30:127 (2005). To safely generate small traces of explosives, genuine material microamounts test specimens (EMPK) can be used. Here, the explosive material (0.5-2.0 mg) is present on a metal foam as described in the EMPK® safety test, Bundesanstalt für Materialforschung und -prüfung, AZ: II.3/4726/04; and certification by Wehrwissenschaftliches Institut für Werk-, Explosiv- and Betriebsstoffe (WIWEB), doc. no.: 330/27454/04; source: http://www.duelsner.de/seiten/deutsch/produkt.html). However, it has been found in studies in a stream of air that these EMPKs are discharged very quickly because of the volatility of the peroxidic explosives and can therefore be used for only a few minutes. This is problematical for, in particular, an exercise in the open with natural air movements. In addition, only very small TATP concentrations can be achieved per EMPK. Explosive samples (microamounts) dissolved in acetonitrile are available as standards from a number of suppliers. For TATP, this is, for example, the AccuStandard company (source: http://www.accustandard.com; catalogue number: M-8330-ADD24, 0.1 mg TATP in 1 ml $CH_3CN$, cost: US\$ 75). The amounts present therein are very small and the added amounts of toxic and volatile solvent are very large, so that use for calibrating gas analytes by means of biological or electronic noses is difficult or prohibitive. The current importance of the TATP problems can be deduced from the large number of published detection methods (as described, for example, in: Detection of Liquid Explosives and Flammable Agents in Connection with Terrorism, Eds: H. Schubert, A. Kuznetsov, NATO Science for Peace and Security Series, Springer, Dordrecht (2008); R. Schulte-Ladbeck et al., Anal. Bioanal. Chem. 386: 559 (2006); R. A. A. Munoz et al., Analyst 132:560 (2007); D. Lu et al., Analyst 131:1279 (2006); D. F. Laine et al., Anal. Chim. Acta 608:56 (2008); R. Schulte-Ladbeck et al., Analyst 127:1152 (2002); M. E. Germain and M. J. Knapp, Inorg. Chem. 47:9748 (2008); S. Malashikhin and N. S. Finney, J. Am. Chem. Soc. 130:12846 (2008); U.S. Pat. No. 6,767,717; E. Sella and D. Shabat, Chem. Commun. 5701 (2008)). To validate these possible detection methods, a TATP source which is safe to handle and displays good performance is required.

The high brisance of peroxidic explosives makes the analysis of substances found extremely dangerous since material has to be taken mechanically from these pulverulent solids for doubt-free identification. Dried peroxidic explosives such as TATP, and in particular HMTD, can be ignited in this way. Such substance finds usually have diesel fuel poured over them and after a certain time the explosive can be collected mechanically without danger. Owing to the complexity of the diesel mixture consisting of several thousand volatile components, later analyses are no longer possible and a forensic evaluation is thus impossible. The provision of a suitable stabilizer is therefore desirable.

Ionic liquids are innovative solvents having a negligible vapor pressure as described in Ionic Liquids in Synthesis, Eds: P. Wasserscheidt, T. Welton, WILEY-VCH, Weinheim (2003), and should therefore not influence the olfactory impression of TATP and other peroxidic explosives. Stabilization of explosives for better processability, especially nitro compounds, has recently been described in US Patent Publication no. 2008/0251169 A1.

The TATP samples handled hitherto have, for safety reasons, only a very low genuine material content. Since TATP is applied there as crystalline material, the brisance of the explosive is still present. The odor simulation of an actual explosive charge of TATP or substance find with a suspicion of TATP can therefore be imitated only unsatisfactorily. In addition, the very small amount of analyte in EMPKs is very quickly discharged in a stream of air. The known test specimens also have a high price (0.5 mg TATP approximately € 40.–). About 10 test specimens are required for test measurements in a stream of air and these are freed of TATP within a few minutes.

SUMMARY

An aspect of the present invention is to provide a neutral ionic liquid (hereinafter referred to as "IL" for short) for stabilizing peroxidic explosives and for producing stable solutions of peroxidic explosives. An alternative aspect of the present invention is to provide a stable composition comprising a solution of a neutral ionic liquid (IL) containing a detectable amount of a peroxidic explosive and a production method therefor. Yet another alternative aspect of the present invention is to provide a use of the aforementioned composition as an odor source, for example, for test measurements, to calibrate detectors and to train explosives sniffer dogs or other biological detection techniques.

In an embodiment, the present invention provides a method of using a neutral ionic liquid to at least one of stabilize a peroxidic explosive and to produce a stable solution of the peroxidic explosive which includes providing the neutral ionic liquid and using the neutral ionic liquid to at least one of stabilize the peroxidic explosive and to produce the stable solution of the peroxidic explosive. The present invention further provides a stable composition which includes a solution of at least one neutral ionic liquid and a detectable amount of a peroxidic explosive, a method of production thereof, and a method of use thereof as an odor sample.

BRIEF DESCRIPTION OF THE FIGURES

The present invention is described in greater detail below on the basis of embodiments and of the drawings in which.

DETAILED DESCRIPTION

Figure 1:
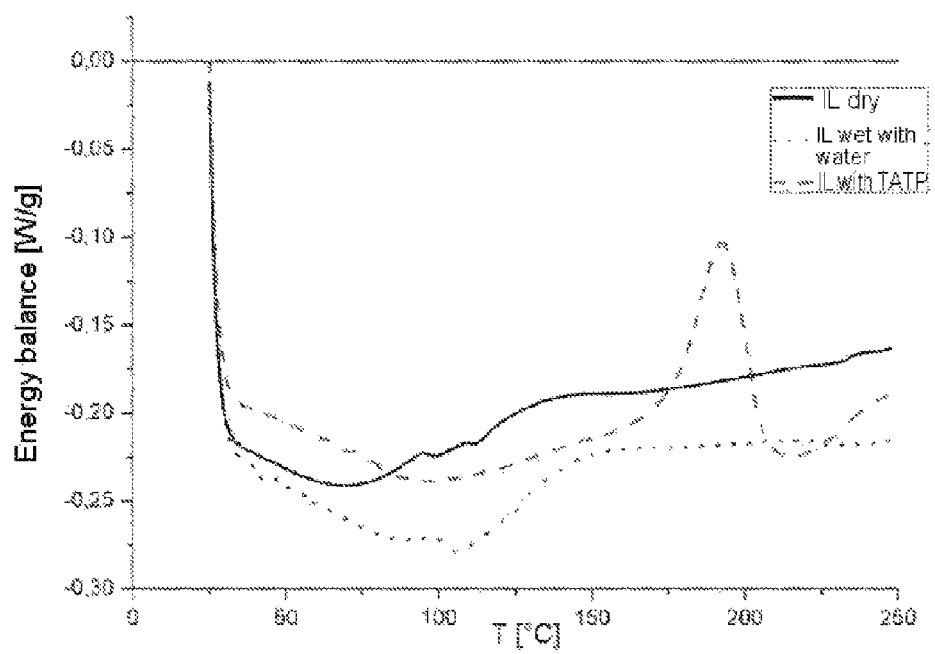
FIG. 1: shows DSC measurement of an ionic liquid (IL) with and without TATP.

It has now been found that dissolution of peroxidic explosives such as TATP or TATP hydrate in specific ionic solvents, as is described in WO 2004/035018, provides a stable and readily handleable form of the explosive TATP. The dramatically reduced mechanical and thermal sensitivity of this solution allows for a simple handling in conventional laboratories with customary equipment. The ionic liquids which have now been examined no longer display any measurable friction and shock sensitivity. Stabilization with the simultaneous option of forensics can also be achieved by means of the ionic liquids. Solutions of ionic liquids in volatile solvents such as dichloromethane can be dripped onto the explosives. The explosives become wetted rapidly and well. Owing to the conductivity of the ionic liquid, electrostatic ignitions are also avoided. The mixture produced no longer displays any friction and shock sensitivity.

In an embodiment of the use and the composition of the present invention, the lipophilic ionic liquids are important since they absorb little water from the surroundings. Since the properties of ionic liquids is determined both by the cations and by the anions, both sides can be varied. Use can be made, for example, of neutral ionic liquids having a low viscosity. Lipophilic anions can, for example, include tetrafluoroborates, triflitimides, perfluoroalkylsulfates, alkylsulfonates, arylsulfonates, perfluoroalkylsulfonates, bisperfluoroalkylsulfonimides, acetates, alkylcarboxylates, isocyanates, isothiochanates, thiosulfates, halides (including iodides, bromides, chlorides and fluorides), borates, phosphates, nitrates and perchlorates, with tetrafluoroborates and triflitimides being particular suitable. Cations can, for example, include N-alkyl-substituted nitrogen heterocycles such as N-alkylpyridinium, N-alkylpyrazinium, N-alkylpyridazinium, N-alkylpyrimidinium and bis-N-alkylimidazolium ions, quaternary ammonium and phosphonium ions, and N,N-dialkylimidazolium and N-alkylpyridinium ions. Specific examples include 1-ethyl-3-methylimidazolium bis(trifluoromethanesulfonimide), 1-butyl-3-methylimidazolium bis(trifluoromethanesulfonimide), 1-hexyl-3-methylimidazolium bis(trifluoromethanesulfonimide), 1-ethyl-3-methylimidazolium tetrafluoroborate, 1-hexyl-3-methylimidazolium tetrafluoroborate, 1-octyl-3-methylimidazolium tetrafluoroborate, 1-decyl-3-methylimidazolium tetrafluoroborate, 1-decyl-3-methylimidazolium tetrafluoroborate, N-hexylpyridinium tetrafluoroborate, N-hexylpyridinium bis(trifluoromethanesulfonimide), N-butyl-3-methylpyridinium tetrafluoroborate and N-butyl-4-methylpyridinium tetrafluoroborate.

Owing to the nonpolar nature of the TATP molecule, lipophilic ionic liquids can, for example, be advantageous. This trend can readily be seen from the solubility of TATP in 1-alkyl-3-methylimidazolium tetrafluoroborates. At least one alkyl radical of the N,N-dialkylimidazolium ion or the N-alkyl radical of N-alkylpyridinium can, for example, be a $C_6$-$C_{16}$-alkyl radical. It is also possible to use mixtures of the ionic liquids mentioned.

Peroxidic explosives for the purposes of the present invention are cyclic peroxides such as triacetone triperoxide (TATP), hexamethylene triperoxide diamine (HMTD), diacetone peroxide, etc., having the structures (I) to (III)

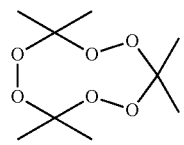

(I)

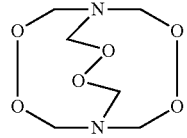

(II)

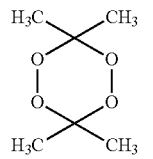

(III)

Diacyl peroxides can, for example, include those of the formula (IV) below, where R is a straight-chain, branched or cyclic, saturated $C_{1-5}$-alkyl radical or a monocyclic or polycyclic aryl radical, where the alkyl and aryl radicals may optionally be substituted by one or more radicals selected from among halogen, nitro, hydroxy and oxo. Examples include diacetyl peroxide and bisbenzoyl peroxide having the structures (Iva) and (Wb),

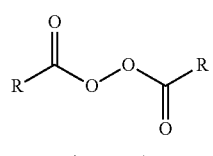

(IV)

in general

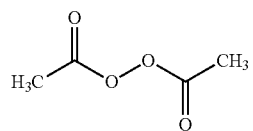

(IVa)

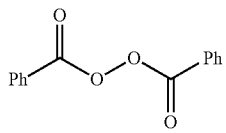

and other easy-to-prepare peroxides such as bis(1-hydroxycyclohexyl) peroxide having the formula (V) below

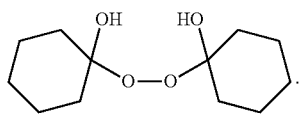

In an embodiment of the use according to the present invention, the IL is used for stabilizing peroxidic explosives (stabilization). The IL can thereby, for example, be used as a mixture with a volatile solvent. Suitable volatile solvents are solvents which do not ignite readily and allow subsequent analysis, including, for example, dichloromethane, chloroform, acetonitrile, ethyl acetate, and dichloromethane. The content of the IL in the volatile solvent can, for example, be from 1 to 25% by weight, for example, from 5 to 15% by weight.

In an embodiment of the use according the present invention, the IL can, for example, be used to produce a stable solution of peroxidic explosives, with the stable solution, for example, being used as an odor source, for example, for test measurements for calibrating detectors and for training explosives sniffer dogs or other biological detection techniques.

In an embodiment of the composition of the present invention, the content of peroxidic explosive can, for example, be from 0.1 to 10% by weight, for example, from 0.5 to 5% by weight, or for example, about 2% by weight, of the composition (balance IL).

In an embodiment of the present invention, the composition can also contain further functional compounds such as dyes or alternative odorous substances which aid identification in addition to IL and peroxidic explosive. In an embodiment, the composition can, for example, consist exclusively of IL and peroxidic explosive.

In an embodiment of the present invention, the production of the composition can, for example, be carried out by adding a peroxide to the ionic liquid and slow dissolution, which can optionally be aided by careful stirring.

The peroxidic explosives solutions in ionic liquids can firstly provide odor sources having a very high and long-lasting intensity since a relatively large amount of TATP is present in the samples. Safe handling is possible since TATP is not present in crystalline form. Excellent thermal and mechanical stability is observed. The nonmeasurable vapor pressure of the ionic liquids does not appreciably falsify the odor profile of the TATP. The main use will be safe odor simulation of a relatively large amount of TATP explosive.

Slight modification of the ionic liquid also makes it possible to provide an active stabilizer for desensitizing quantities of TATP and allows:
safe handling of peroxidic explosives in ionic liquids;
production of odor samples of peroxidic explosives by dissolution in ionic liquids;
production of test specimens having an intensive odor signature;
simulation of large IEDs by evaporation of genuine materials from ionic liquids; and
stabilizing degradation of the peroxidic explosives by means of ionic liquids having a reducing action.

In an embodiment, the composition of the present invention provides a strong explosives (TATP) odor signature, simulation of real scenarios, explosives (TATP) desensitization, genuine material test specimens, explosive, peroxides, ionic liquid, odor bodies, safe handling. The composition can furthermore be used for test measurements and calibration of explosives (TATP) detectors and also explosives (TATP) detection systems under conditions of real scenarios of a terrorist threat (bomb based on TATP), training of explosives sniffer dogs or other biological detection techniques.

The present invention is illustrated by the following examples, which do not, however, restrict the scope of protection:

EXAMPLES

Production of an Ionic Liquid Saturated with Peroxide/TATP

From 20 to 50 ml of the ionic liquid is placed in a 250 ml flask with a magnetic stirrer bar. The flask can, for example, have a wide opening so that pulverulent material can be added easily and the bottom should have a conical shape in order to aid decantation of the liquid after dissolution. The stirrer bar and the magnetic stirrer should have sufficiently strong magnetic fields so that viscous suspensions can be mixed reliably at a high speed of rotation. The flask is clamped on a magnetic stirrer with stand close to the magnet. The stirrer is set to the highest possible speed of rotation which still allows the stirrer bar to follow the rotation reliably. In practice, the speed of rotation is from 700 to 1000 rpm. 500 mg of the peroxide/triacetone peroxide hydrate (TATP) is added and the flask is closed so as to be gastight. The ground glass stopper is carefully sealed by means of high vacuum grease and clamped shut so that no peroxide can escape during dissolution. The mixture is stirred until the peroxide has completely dissolved. This generally takes from 8 to 12 hours. If the peroxide has not been dissolved completely, mixing is continued for at least another 48 hours to provide that the solution is saturated. If the peroxide has been dissolved completely, an additional 500 mg of TATP is added and mixing is again continued either until complete dissolution or for 12 hours. This procedure is repeated until undissolved peroxide remains in the solution. The mixture is then stirred for another 48 hours.

When the solutions are saturated, the stirrer is switched off and the solutions are allowed to stand for at least 24 hours. During this time, the excess peroxide separates out either on the surface or on the bottom, depending on the density of the liquid. The clear liquid is slowly drawn off slowly by means of a pipette and dispensed into securely closed containers. The peroxide residues in the dissolution flask are disposed by means of 5% sodium dithionite in an acetone/water mixture (70:30, by weight).

It should be noted that filtration is generally not possible for the viscous ionic liquids without large losses of material. The excess peroxide therefore has to be separated off by decantation or centrifugation. Small amounts of very small crystals remain in the liquid. This very small excess ensures that the TATP solutions remain saturated even when small amounts of acetone peroxide escape, for example, through the seals of the containers. The crystal residues do not represent a hazard due to increased sensitivity because they are present in only such small amounts. The properties of the TATP-containing ionic liquids are summarized in Table 1 below.

TABLE 1

Overview of the Solubility of TATP in Selected Ionic Liquids (IL)

| Ionic liquid (IL) | M (IL) [g/mol] | rel. TATP integral | c[TATP] (w %) |
|---|---|---|---|
| 1-Ethyl-3-methylimidazolium bis(trifluoro-methanesulfonimide) | 391.31 | 0.12 | 0.38 |
| 1-Butyl-3-methylimidazolium bis(trifluoro-methanesulfonimide) | 419.36 | 0.32 | 0.94 |
| 1-Hexyl-3-methylimidazolium bis(trifluoro-methanesulfonimide) | 447.42 | 0.31 | 0.86 |
| 1-Ethyl-3-methylimidazolium tetrafluoroborate | 197.97 | 0.02 | 0.12 |
| 1-Hexyl-3-methylimidazolium tetrafluoroborate | 254.08 | 0.27 | 1.31 |
| 1-Octyl-3-methylimidazolium tetrafluoroborate | 282.13 | 0.49 | 2.14 |
| 1-Hexyl-3-methylimidazolium iodide | 294.18 | 0.09 | 0.38 |
| 1-Decyl-3-methylimidazolium tetrafluoroborate | 310.18 | 0.32 | 1.27 |
| N-Hexylpyridinium tetrafluoroborate | 251.07 | 0.09 | 0.44 |
| N-Hexylpyridinium bis(trifluoromethanesulfonimide) | 444.41 | 0.33 | 0.92 |
| N-Butyl-3-methylpyridinium tetrafluoroborate | 237.05 | 0.06 | 0.31 |
| N-Butyl-4-methylpyridinium tetrafluoroborate | 237.05 | 0.00 | 0.00 |

Determination of the TATP Content Via NMR Spectroscopy

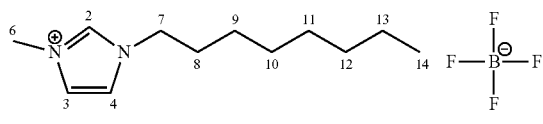

1-Octyl-3-methylimidazolium tetrafluoroborate $^1$H-NMR (400 MHz, DMSO-d6): δ=0.85 (t, 3H, H 14, $^3$J=8.0 Hz), 1.25 (m, 10H, H 9-13), 1.36 (s, 0.49H, CH$_3$ TATP), 1.79 (m, 2H, H 8), 3.85 (s, 3H, H 6), 4.15 (t, 2H, H 7, $^3$J=8.0H), 7.70 (m, 2H, H3-4), 9.04 (s, 1H, H 2).

For the concentration determination, the ratio of the TATP signal at 1.36 ppm to the signal of the methyl group of imidazole at 3.85 ppm is formed.

$$c(\% \text{ by weight of TATP}) = [M(\text{TATP}) \cdot (\text{TATP signal}/6) \cdot 100]/M(\text{IL}) \quad (1)$$

where M (TATP)=222.2 g/mol.

Determination of Thermal Stability

It can be seen from the DSC measurements shown in FIG. 1 that the pure ionic liquid remains stable up to at least 250° C. The ionic liquid admixed with TATP displays an exothermic reaction in the range from 165° C. to 205° C., with a decomposition maximum at 190° C. The decomposition extends over a temperature range of about 40° C., which indicates a slow, nonexplosive, decomposition. The increasing energy demand between 25° C. and 100° C. is due to dissolved water which is first evaporated. This can be seen for the water-doped ionic liquid. This is confirmed by a control experiment using ionic liquid which is wet with water.

The TATP in ionic liquid is a thermally handleable, nonexplosive and safe form of this explosive.

Determination of Evaporation Rates

Figure 2:
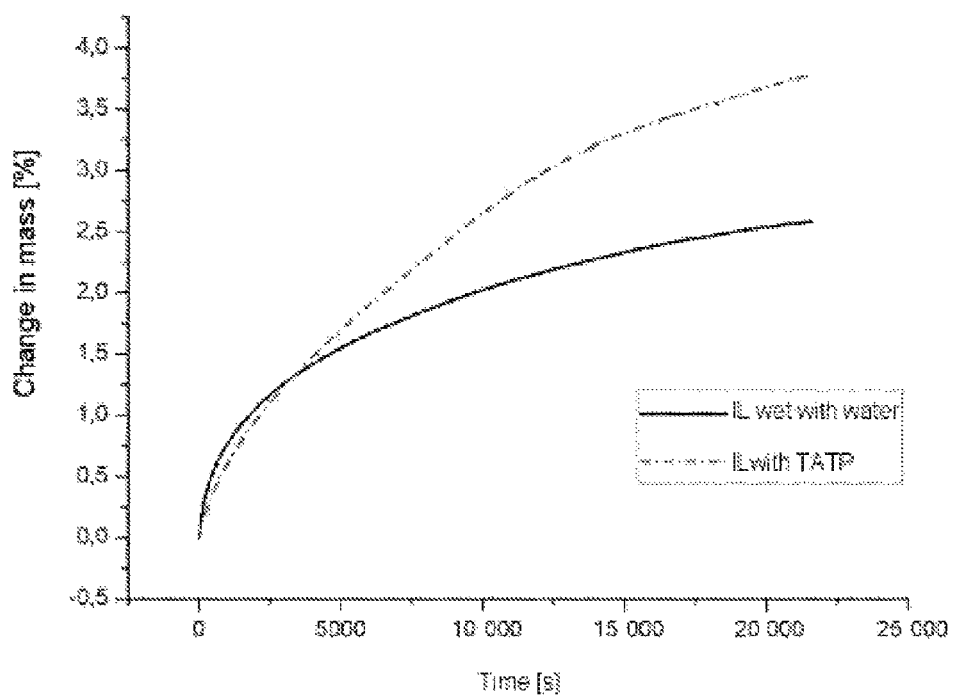
FIG. 2: shows TGA measurements of an ionic liquid (IL) with and without TATP.

The TGA measurements summarized in FIG. 2 show that the TATP and the water absorbed due to the ionic character are desorbed over a long period of time. The slow evaporation rate should make the TATP-doped ionic liquid suitable as an exercise source for various detection methods. The large linear range of the TATP sample promises a long and reliable period of use in a stream of air.

Method of Saturating the IL with HMTD

From 20 to 50 ml of the ionic liquid is placed in a 250 ml flask with a magnetic stirrer bar. The flask can, for example, have a wide opening so that pulverulent material can be added easily and the bottom should have a conical shape in order to aid decantation of the liquid after dissolution. The flask is thermostated to 30° C. by means of a water bath. The stirrer bar and the magnetic stirrer should have sufficiently strong magnetic fields so that even viscous suspensions can be reliably mixed at a high speed of rotation. The flask is clamped on a magnetic stirrer with stand close to the magnet. The stirrer is set to the highest possible speed of rotation which still allows the stirrer bar to follow the rotation reliably. In practice, the speed of rotation is from 700 to 1000 rpm. 500 mg of HMTD is added and the flask is closed so as to be gastight. The ground glass stopper is carefully sealed by means of high vacuum grease and clamped shut so that no peroxide can escape during dissolution. HMTD additions are repeated at 24 hour intervals until no more HMTD dissolves. The suspension is then stirred for another one week before decantation is carried out in a manner analogous to the saturation with TATP. The content of HMTD is determined by NMR spectroscopy.

Illustrative Determination of HMTD Content

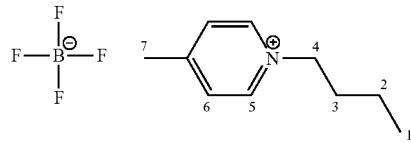

N-Butyl-4-methylpyridinium tetrafluoroborate: $^1$H-NMR (400 MHz, DMSO-d6): δ=0.88 (t, 3H, H1, $^3$J$_{1,2}$=8.0 Hz), 1.25 (tq, 2H, H 2, $^3$J$_{2,1}$=8.0 Hz, $^3$J$_{2,3}$=8.0 Hz), 1.87 (tt, 2H, H 3, $^3$J$_{3,2}$=8.0 Hz, $^3$J$_{3,4}$=6.0 Hz), 2.60 (s, 3H, H 7), 4.52 (t, 2H, H 4, $^3$J$_{4,3}$=6.0 Hz), 4.65 (d, 0.35H, H$_A$ HMTD, $^3$J$_{HA,HB}$=14.0 Hz), 4.77 (d, 0.35H, H$_B$ HMTD, $^3$J$_{HB,HA}$=14.0 Hz), 7.95 (d, 2H, H 6, $^3$J$_{6,5}$=4.0 Hz), 8.86 (d, 2H, H 5, $^3$J$_{5,6}$=8.0 Hz).

To determine the concentration of HMTD, the ratio of the sum of the integrals at 4.65 ppm and 4.77 ppm (corresponds to 12 protons) to the signal of the methyl group of the alkyl chain at 0.88 ppm (corresponds to 3 protons) is formed. For simplification, the integrals are modified even during the evaluation so that a value of 3 is obtained for the integral of the IL methyl protons (0.88 ppm).

$$c(HMTD) = \frac{HMTD\ \text{signal}/12}{IL\ \text{signal}/3} * \frac{M(HMTD)}{M(IL)}$$

Owing to the normalization to the methyl protons of the IL, the left-hand lower term becomes 1. For presentation in %, the volume is multiplied by 100.

$$c(HMTD)=[M(HMDT) \cdot (HMTD\ \text{signal}/12) \cdot 100]/M(IL) \quad (1),$$

where M (HMTD)=208.10 g/mol.

TABLE 2

Overview of the Solubility of HMTD in Ionic Liquids (IL)

| Ionic liquid (IL) | M (IL) [g/mol] | rel. HMTD integral[a] | c[HMTD] (w %) |
|---|---|---|---|
| 1-Ethyl-3-methylimidazolium bis(trifluoromethanesulfonimide) | 391.31 | 0.54 | 2.39 |
| 1-Butyl-1-methylpyrolidinium bis(trifluoromethanesulfonimide) | 422.41 | 0.55 | 2.26 |
| N-Hexylpyridinium bis(trifluoromethanesulfonimide) | 444.41 | 0.54 | 2.11 |
| N-Butyl-3-methylpyridinium tetrafluoroborate | 237.05 | 0.23 | 1.68 |
| N-Butyl-3-methylpyridinium tetrafluoroborate | 237.05 | 0.17 | 1.24 |
| N-Butyl-4-methylpyridinium tetrafluoroborate | 237.05 | 0.70 | 5.12 |
| N-Hexylpyridinium tetrafluoroborate | 251.07 | 0.04 | 0.28 |
| 1-Hexyl-3-methylimidazolium bis(trifluoromethanesulfonimide) | 447.42 | 1.17 | 4.53 |
| 1-Ethyl-3-methylimidazolium diethylphosphate | 264.26 | 0.14 | 0.92 |
| 1-Ethyl-3-methylimidazolium methanesulfonate | 206.26 | 0.48 | 4.04 |
| 1-Butyl-1-methylpyrrolidinium trifluoromethanesulfonate | 291.34 | 0.17 | 1.01 |

[a]To calculate the relative signal, the integrals in the NMR are set to 3 by normalization of a methyl group of the IL. The relative signal is the sum of the two HMTD proton signals after this normalization and thus represents the integral of the 12 HMTD protons per molecule of IL (see above).

Stabilization of Peroxidic Explosives

Stabilization solution: 10% of 1-hexyl-3-methylimidazolium bis(trifluoromethylsulfonimide) in dichloromethane Before Stabilizing Treatment Sensitivity to friction: HMTD 0.05 N—100% ignition; TATP 0.2 N—100% ignition.

Impact sensitivity: HMTD 0.2 J—100% ignition, TATP 0.5 J—100% ignition.

Stabilization experiments: 100 mg of explosive are moistened with 200 mg of 10% stabilization solution, allowed to dry for 15 minutes and then measured. Within the measurement range, the two stabilized explosives could no longer be ignited: >1 J impact sensitivity and >30 N sensitivity to friction.

The present invention is not limited to embodiments described herein; reference should be had to the appended claims.

What is claimed is:

1. A method of using a neutral ionic liquid to at least one of stabilize a peroxidic explosive and to produce a stable solution of the peroxidic explosive, the method comprising:
   providing the neutral ionic liquid; and
   dissolving the peroxidic explosive in the neutral ionic liquid so as to obtain a dissolved solution to at least one of stabilize the peroxidic explosive and to produce the stable solution of the peroxidic explosive,
   wherein, the peroxidic explosive comprises from about 0.1 to about 10% by weight of the dissolved solution.

2. The method as recited in claim 1, wherein neutral ionic liquid is selected from at least one of:
   tetrafluoroborate, triflitimide, perfluoroalkylsulfate, alkylsulfonate, arylsulfonate, perfluoroalkylsulfonate, bisperfluoroalkylsulfonimide, acetate, alkylcarboxylate, isocyanate, isothiocyanate, thiosulfate, a halide, a borate, a phosphate, a nitrate, a quaternary ammonium, a phosphonium, and a perchlorate salt of an N-alkyl-substituted nitrogen heterocycle, such as N-alkylpyridinium, N-alkylpyrazinium, N-alkylpyridazinium, N-alkylpyrimidinium and bis-N-alkylimidazolium.

3. The method as recited in claim 2, wherein the neutral ionic liquid is selected from tetrafluoroborates and bisperfluoroalkylsulfonimides of 1,3-bis-N-alkylimidazolium and N-alkylpyridinium.

4. The method as recited in claim 2, wherein the neutral ionic liquid is selected from at least one of:
   1-ethyl-3-methylimidazolium bis(trifluoromethanesulfonimide);
   1-butyl-3-methylimidazolium bis(trifluoromethanesulfonimide);
   1-hexyl-3-methylimidazolium bis(trifluoromethanesulfonimide);
   1-ethyl-3-methylimidazolium tetrafluoroborate;
   1-hexyl-3-methylimidazolium tetrafluoroborate;
   1-octyl-3-methylimidazolium tetrafluoroborate;
   1-decyl-3-methylimidazolium tetrafluoroborate;
   N-hexylpyridinium tetrafluoroborate;
   N-hexylpyridinium bis(trifluoromethanesulfonimide);
   N-butyl-3-methylpyridinium tetrafluoroborate; and
   N-butyl-4-methylpyridinium tetrafluoroborate.

5. The method as recited in claim 1, wherein the peroxidic explosive is at least one of:
   triacetone triperoxide (TATP);
   hexamethylene triperoxide diamine (HMTD);
   diacetone peroxide; and
   a diacyl peroxide of the formula R(C=O)—OO—(C=O)R, wherein R is a straight-chain, a branched or a cyclic, saturated $C_{1-5}$-alkyl radical, or a monocyclic or a polycyclic aryl radical, and wherein the alkyl and aryl radicals may optionally be substituted by one or more radicals selected from a halogen, a nitro, a hydroxyl, an oxo and a peroxide such as bis(1-hydroxycyclohexyl) peroxide.

6. The method of using as recited in claim 1, wherein the neutral ionic liquid is used to stabilize the peroxidic explosive, and the ionic liquid is provided as a mixture with a volatile solvent.

7. The method of using as recited in claim 6, wherein the volatile solvent is provided as a solvent which does not ignite readily so as to allow for a subsequent analysis.

8. The method of using as recited in claim 7, wherein the volatile solvent is at least one of dichloromethane, chloroform, acetonitrile and ethyl acetate.

9. The method of using as recited in claim 1, wherein the neutral ionic liquid is used to produce the stable solution of the peroxidic explosive, and wherein the method further comprises:
   providing the stable solution with an odor source; and
   using the stable composition and the odor source to at least one of provide a test measurement to calibrate a detector, train an explosives sniffer dog, and as a biological detection technique.

* * * * *